US009295665B2

(12) United States Patent
Wang et al.

(10) Patent No.: US 9,295,665 B2
(45) Date of Patent: Mar. 29, 2016

(54) INHIBITION OF NEOVASCULARIZATION BY SIMULTANEOUS INHIBITION OF PROSTANOID IP AND EP4 RECEPTORS (71) Applicant: ALLERGAN, INC., Irvine, CA (US)

(72) Inventors: Jenny W. Wang, Irvine, CA (US); David F. Woodward, Lake Forest, CA (US)

(73) Assignee: ALLERGAN, INC., Irvine, CA (US)

( * ) Notice: Subject to any disclaimer, the term of this patent is extended or adjusted under 35 U.S.C. 154(b) by 2 days.

(21) Appl. No.: 14/197,948

(22) Filed: Mar. 5, 2014

(65) Prior Publication Data

US 2014/0275200 A1 Sep. 18, 2014

Related U.S. Application Data (60) Provisional application No. 61/778,049, filed on Mar. 12, 2013.

(51) Int. Cl.
*A61K 31/403* (2006.01)
*A61K 31/343* (2006.01)
*A61K 45/06* (2006.01)
*A61K 31/4965* (2006.01)
*A61K 31/195* (2006.01)
*A61K 31/275* (2006.01)
*A61K 31/395* (2006.01)
*A61K 31/4166* (2006.01)
*A61K 31/4196* (2006.01)
*A61K 31/424* (2006.01)
*A61K 31/5375* (2006.01)
*A61K 31/557* (2006.01)

(52) U.S. Cl.
CPC ............. *A61K 31/403* (2013.01); *A61K 31/195* (2013.01); *A61K 31/275* (2013.01); *A61K 31/343* (2013.01); *A61K 31/395* (2013.01); *A61K 31/4166* (2013.01); *A61K 31/4196* (2013.01); *A61K 31/424* (2013.01); *A61K 31/4965* (2013.01); *A61K 31/5375* (2013.01); *A61K 31/557* (2013.01); *A61K 45/06* (2013.01)

(58) Field of Classification Search
CPC ........................... A61K 31/403; A61K 31/343
USPC ....................................................... 514/411
See application file for complete search history.

(56) References Cited

U.S. PATENT DOCUMENTS

| | | | |
|---|---|---|---|
| 4,861,760 A | 8/1989 | Mazuel et al. |
| 4,911,920 A | 3/1990 | Jani et al. |
| 5,212,162 A | 5/1993 | Missel et al. |
| 5,403,841 A | 4/1995 | Lang et al. |
| 6,184,242 B1 | 2/2001 | Bley et al. |
| 6,417,186 B1 | 7/2002 | Jahangir |
| 6,569,860 B2 | 5/2003 | Lopez-Tapia |
| 6,693,098 B2 | 2/2004 | Cournoyer et al. |
| 6,903,086 B2 | 6/2005 | Lopez-Tapia |
| 6,998,414 B2 | 2/2006 | Keitz et al. |
| 7,056,903 B2 | 6/2006 | Cournoyer et al. |
| 8,003,661 B2 | 8/2011 | Burch et al. |
| 8,013,159 B2 | 9/2011 | Belley et al. |
| 8,158,671 B2 | 4/2012 | Boyd et al. |
| 2002/0091147 A1 | 7/2002 | Jahangir |

FOREIGN PATENT DOCUMENTS

| | | |
|---|---|---|
| EP | 0902018 A2 | 3/1999 |
| WO | 0168591 A1 | 9/2001 |
| WO | 0240453 A1 | 5/2002 |
| WO | 0250033 A1 | 6/2002 |
| WO | 02070500 A1 | 9/2002 |
| WO | 02070514 A1 | 9/2002 |

OTHER PUBLICATIONS

Green, Richard W., Histopathology of age-related macular degeneration, Molecular Vision, 1999, 5:27.
Resnikoff et al., Global data on visual impairment in the year 2002, Bulletin of the World Health Organization, 2004; 82: 844-851.
Ashton, Norman, Retinal Vascularization in Health and Disease, Proctor Award Lecture of the Association for Research in Ophthalmology, 1957, pp. 7-17.
Shimizu et al., Midperipheral Fundus Involvement in Diabetic Retinopathy, Ophthalmology, Jul. 1981, vol. 88, No. 7, pp. 601-612.
Shweiki et al., Vascular endothelial growth factor induced by hypoxia may mediate hypoxia-initiated angiogenesis, Nature Publishing Group, vol. 359, Oct. 29, 1992, pp. 843-845.
Forsythe et al., Activation of vascular endothelial growth factor gene transcription by hypoxia-inducible factor 1, Mol. Cell. Biol., 1996, 16 (9), pp. 4604-4613.
Adamis et al., Increased Vascular Endothelial Growth Factor Levels in the Vitreous of Eyes With Proliferative Diabetic Retinopathy, American Journal of Ophthalmology, 118, 1994, pp. 445-450.
Aiello et al., Vascular Endothelial Growth Factor in Ocular Fluid of Patients with Diabetic Retinopathy and Other Retinal Disorders, The New England Journal of Medicine, Dec. 1, 1994, pp. 1480-1487.
Malecaze et al., Detection of Vascular Endothelial Growth Factor Messenger RNA and Vascular Endothelial Growth Factor-like Activity in Proliferative Diabetic Retinopathy, Arch. OphthalmoL, vol. 112, Nov. 1994, pp. 1476-1482.
Miller et al., Vascular Endothelial Growth Factor/Vascular Permeability Factor is Temporally and Spatially Correlated with OCular Angiogenesis in a Primate Model, American Journal of Pathology, vol. 145, No. 3, Sep. 1994, pp. 574-584.
Pierce et al., Vascular Endothelial Growth Factor/Vascular Permeability Factor Expression in a Mouse Model or Retinal Neovascularization, Proc. Natl. Acad. Sci. USA, vol. 92, Jan. 1995, pp. 905-909.
Okamoto et al., Transgenic Mice with Increased Expression of Vascular Endothelial Growth Factor in the Retina, American Journal of Pathology, vol. 151, No. 1, Jul. 1997, pp. 281-291.

(Continued)

Primary Examiner — Raymond Henley, II
(74) Attorney, Agent, or Firm — Jonathan Bass (57) ABSTRACT There are provided inter alia methods and compounds useful for decreasing neovascularization (e.g., choroidal neovascularization) in a subject in need thereof.

15 Claims, 6 Drawing Sheets (56) References Cited

OTHER PUBLICATIONS

Tobe et al., Evolution of Neovascularization in Mice with Overexpression of Vascular Endothelial Growth Factor in Photoreceptors, Investigative Ophthalmology & Visual Science, vol. 39, No. 1, Jan. 1998, pp. 180-188.

Robinson et al., Oligodeoxynucleotides Inhibit Retinal Neovascularization in a Murine Model of Proliferative Retinopathy, Proc. Natl. Acad. Sci. USA, vol. 93, May 1996, pp. 4851-4856.

Aiello et al., Suppression of Retinal Neovascularization in vivo by Inhibition of Vascular Endothelial Growth Factor (VEGF) Using Soluble VEGF-receptor Chimeric Proteins, Proc. Natl. Acad. Sci. USA, vol. 92, Nov. 1995, pp. 10457-10461.

Adamis et al., Inhibition of Vascular Endothelial Growth Factor Prevents Retinal Ischemia-Associated Iris Neovascularization in a Nonhuman Primate, Arch. Ophthalmol. vol. 114, Jan. 1996, pp. 66-71.

Spilsbury et al., Overexpression of Vascular Endothelial Growth Factor (VEGF) in the Retinal Pigment Epithelium Leads to the Development of Choroidal Neovascularization, American Journal of Pathology, vol. 157., No. 1, Jul. 2000, pp. 135-144.

Boie et al., Cloning and Expression of a cDNA for the Human Prostanoid IP Receptor, The Journal of Biological Chemistry, vol. 269, No. 16, Apr. 22, 1994, pp. 12173-12178.

Berge et al., Pharmaceutical Salts, Journal of Pharmaceutical Sciences, vol. 66, No. 1, Jan. 1977, pp. 1-19.

Fingl et al., Basis of Therapeutics, Fifth Edition, 1975, pp. 1-52.

Francois et al., Neovascularization After Argon Laser Photocoagulation of Macular Lesions, Am. J. Ophthalmol. vol. 79, pp. 206-210.

Edelman et al., Quantitative Image Analysis of Laser-induced Choroidal Neovascularization in Rat, Exp. Eye Res., vol. 71, 2000, pp. 523-533.

Goody et al., Optimization of laser-induced choroidal neovascularization in African green monkeys, Experimental Eye Research, vol. 92, 2011, pp. 464-472.

Michaelson, I.C., The Mode of Development of the Vascular System of the Retina, With Some Observations on its Significance for Certain Retinal Diseases, Ophthalmological Society of the United Kingdom, Session 68, Apr. 1948. pp. 137-180.

Wilson et al., GW627368X ({N-{2-[4-(4,9-diethoxy-1-oxo-1,3-dihydro-2Hbenzo[f]isoindol-2-yl)phenyl]acetyl} benzene sulphonamide): a novel, potent and selective prostanoid EP4 receptor antagonist, British Journal of Pharmacology, 148, 2006, pp. 326-339.

Pe'er, J., et al., Hypoxia-Induced Expression of Vascular Endothelial Growth Factor by Retinal Cells is a Common Factor in Neovascularizing Ocular Diseases, Lab. Invest. 1995, 72: 638-645 (6).

Plate, K.H., Vascular endothelial growth factor is a potential tumour angiogensis factor in human gliomas in vivo, Nature 1992, 359: 845-848.

INHIBITION OF NEOVASCULARIZATION BY SIMULTANEOUS INHIBITION OF PROSTANOID IP AND EP4 RECEPTORS

CROSS REFERENCE TO RELATION APPLICATION

This application claims the benefit of U.S. Provisional Patent Application Ser. No. 61/778,049, filed Mar. 12, 2013, the entire disclosure of which is incorporated herein by reference.

BACKGROUND OF THE INVENTION

Neovascularization refers generally to the formation of functional vascular (e.g., microvascular) networks. The formation may involve proliferation of blood vessels in tissue not normally containing blood vessels, or of blood vessels of a different type than found in the neovascularized tissue under normal physiological conditions. For example, choroidal neovascularization (CNV) involves the invasion of new blood vessels at the choroid. CNV can involve abnormalities in Bruch's membrane forming the innermost layer of the choroid. The resulting neovascular tissue can cause physical separation of the laminar structure of the retina and destruction of normal retinal tissue in turn causing leakage, bleeding, and blindness. Accordingly, CNV is associated with a variety of diseases of the eye including age-related macular degeneration (AMD). For example, in the so-called "wet" form of AMD, CNV develops in the choriocapillaris and subretinal space, disrupting the retinal pigment epithelium (RPE) which results in significant loss of the central vision. See e.g., Green, 1999, *Mol. Vis.* 5:27. Indeed, AMD is a leading cause of blindness in older populations of developed countries. See e.g., Resnikoff et al., 2004, *Bull. World Health Organ.* 82:844-851.

Occlusion of retinal vessels leading to ischemia and/or hypoxia is common in CNV. See e.g., Michaelson I., 1948, *Trans Ophthalmol Soc UK.* 68:137-180; Ashton N., 1957, *Am J Ophthalmol.* 44:7-17; 6. Shimizu K, et al., 1981, *Ophthalmology* 88:601-612. Extensive evidence on the involvement of Vascular Endothelial Growth Factor (VEGF) has been provided. For example, VEGF is upregulated in hypoxia, and levels of VEGF are increased with ischemic retinopathy. See e.g., Shweiki D, et al., 1992, *Nature* 359:843-845; Plate K H, et al., 1992, *Nature* 359:845-848; Forsythe J A, et al., 1996, *Mol Cell Biol.* 16:4604-4613; Adamis A P, et al., 1994, *Am J Ophthalmol* 118:445-450; 12. Aiello L P, et al., 1994, *N Engl J Med.* 331:1480-1487; Malecaze F, et al., 1992, *Arch Ophthalmol.* 112:1476-1482; Pe'er J, et al., 1995, *Lab Invest.* 72:638-645; Miller J W, et al., 1994, *Am J Pathol.* 145:574-584; Pierce E A, et al., 1995, *Proc Natl Acad Sci USA.* 92:905-909. Indeed, increased expression of VEGF in retinal photoreceptors of transgenic mice stimulates neovascularization within the retina, and VEGF antagonists partially inhibit retinal neovascularization in animal models. See e.g., Okamoto N, et al. 1997, *Am J Pathol.* 151:281-291; Tobe T, et al., 1998, *Invest Ophthalmol Vis Sci.* 39:180-188; Aiello L P, et al., 1995, *Proc Natl Acad Sci USA.* 92:10457-104611 Robinson G S, et al., 1996, *Proc Natl Acad Sci USA.* 93:4851-4856; Adamis A P, et al., 1996, *Arch Ophthalmol.* 114:66-71. Moreover, overexpression of VEGF in the subretinal space results in neovascularization of the choroidal membranes and death of the overlying photoreceptor cells. See e.g., Spilsbury, K., et al., 2000, *Am. J. Pathology* 157:135-144.

Accordingly, there is a need to decrease neovascularization (e.g., CNV) in subjects in need thereof. There are provided herein methods and compounds useful, inter alia, to decrease neovascularization.

BRIEF SUMMARY OF THE INVENTION

In a first aspect, there is provided a method for decreasing neovascularization in a subject in need thereof. The method includes administering to the subject an effective amount of an IP receptor antagonist in combination with an effective amount of an $EP_4$ receptor antagonist, thereby decreasing the neovascularization.

In another aspect, there is provided a pharmaceutical composition including an IP receptor antagonist in combination with an $EP_4$ receptor antagonist, further in combination with a pharmaceutically acceptable excipient.

In another aspect, there is provided an ophthalmic pharmaceutical formulation including an IP receptor antagonist and an $EP_4$ receptor antagonist, further in combination with an ophthalmic pharmaceutically acceptable excipient.

BRIEF DESCRIPTION OF THE DRAWINGS

FIG. 1.

FIG. 2. FIG. 2 depicts the changes in impedance of cells in response to $EP_4$ receptor agonist (FIG. 2A) and IP receptor agonist (FIG. 2B) in human retinal microvascular endothelial cells by Cellular Dielectric Spectroscopy. The data showed that $EP_4$ and IP receptors are functional receptors in human retinal microvascular endothelial cells.

FIG. 3. Simultaneous blockade of IP and $EP_4$ receptors is superior to IP receptor blockade alone in laser-induced choroidal neovascularization (CNV). Vehicle is 50% propylene glycol in $H_2O$. $EP_4$ antagonist is Formula IV. IP antagonist is Formula II. FIG. 3C: CNV area (µm²) lesion vs. lesion comparison, n=36. Histogram ordering (FIGS. 3A-3C, left to right): Vehicle; $EP_4$ Antagonist; IP Antagonists; combination $EP_4$ Antagonist+IP Antagonist.

DETAILED DESCRIPTION OF THE INVENTION

I. Methods

In a first aspect, there is provided a method for decreasing neovascularization in a subject in need thereof. The method includes administering to the subject an effective amount of an IP receptor antagonist in combination with an effective amount of an $EP_4$ receptor antagonist, thereby decreasing the neovascularization.

The terms "subject," "patient" and the like refer, except where indicated otherwise, to mammals such as humans and non-human primates, as well as rabbits, rats, mice, goats, pigs, and other mammalian species. The term does not necessarily indicate that the subject has been diagnosed with a particular disease but typically refers to an individual under medical supervision. In one embodiment, the subject is a human. The phrases "subject in need" and the like refer to a subject having a perceived or diagnosed disease or condition (e.g., age-related macular degeneration).

The term "neovascularization" refers in the usual and customary sense to the formation of vasculature, such as de novo formation of functional microvascular networks having red blood cell perfusion. In one embodiment, neovascularization is of the choroid layer of the eye. Accordingly, the terms "choroidal neovascularization," "CNV" and the like refer to the formation of vasculature in the choroid, such as functional microvascular networks having red blood cell perfusion within or associated with the choroid. Thus, in one embodiment, there is provided a method for decreasing choroidal neovascularization in a subject in need thereof. The method includes administering to the subject an effective amount of an IP receptor antagonist in combination with an effective amount of an $EP_4$ receptor antagonist, thereby decreasing the neovascularization.

The terms "IP receptor," "prostaglandin $I_2$ receptor," "prostacyclin receptor," "PTGIR" and the like refer in the usual and customary sense to a receptor for prostacyclin (i.e., $PGI_2$, prostaglandin $I_2$). The natural receptors are members of the G protein-coupled receptor gene superfamily. Upon activation, an IP receptor typically causes an elevation in intracellular cAMP via direct stimulation of adenylate cyclase. Human IP receptors are well-known in the art and are discussed in detail, for example, in Boie et al., 1994, *J. Biol. Chem.* 269:12173-12178.

Useful IP receptor antagonists include, for example, those set forth in: EP 0 902 018 A2 (e.g., 2-(arylphenyl)amino-imidazoline derivatives which are IP receptor antagonists); U.S. Pat. No. 6,184,242 (e.g., 2-(substituted-phenyl)amino-imidazoline derivatives); WO 02/070514 (e.g., alkoxycarbonylamino heteroaryl carboxylic acid derivatives); WO 02/070500 (e.g., alkoxycarbonylamino benzoic acid or alkoxycarbonylamino tetrazolyl phenyl derivatives); WO 02/40453 (e.g., substituted 2-phenylaminoimidazoline phenyl ketone derivatives); WO 01/68591 (e.g., carboxylic acid derivatives); U.S. Pat. No. 6,417,186; U.S. Pat. No. 6,569,860; U.S. Pat. No. 6,903,086; U.S. Pat. No. 6,693,098; U.S. Pat. No. 6,998,414 and U.S. Pat. No. 7,056,903.

Additional IP receptor antagonists for use in the methods set forth herein include the compounds described as follows. The structure of selexipag (2-(4-((5,6-diphenylpyrazin-2-yl)(isopropyl)amino) butoxy)-N-(methylsulfonyl)acetamide) is:

and includes pharmaceutically acceptable salts of the above. The structure of 2-(3-(4,5-diphenyl-[2,4'-bioxazol]-5'-yl)phenoxy)acetic acid is:

and includes pharmaceutically acceptable salts of the above. The structure of 3-(4-fluorophenyl)-2-((5-(4-fluorophenyl)benzofuran-2-yl)(methoxycarbonyl)amino)propanoic acid is:

and includes pharmaceutically acceptable salts of the above. The structure of (R)-3-phenyl-2-((((5-phenylbenzofuran-2-yl)methoxy)carbonyl)amino)propanoic acid is:

and includes pharmaceutically acceptable salts of the above.

Other useful IP receptor antagonists include compounds denoted as Formulas I and II below. The structure of Formula I is:

and includes pharmaceutically acceptable salts of the above. The structure of Formula II is:

and includes pharmaceutically acceptable salts of the above.

An example of an IP receptor agonist useful in the experimental work described herein is cicaprost. The structure of cicaprost (Formula III) is:

(III)

Cicaprost and includes pharmaceutically acceptable salts of the above.

The terms "EP$_4$ receptor," "prostaglandin E$_4$ receptor" and the like refer, in the usual and customary sense, to a receptor for prostaglandin E$_2$ (PGE$_2$). The receptor is a G-protein coupled receptor, which has been shown, inter alia, to mediate PGE$_2$ induced expression of early growth response 1, to regulate the level and stability of cyclooxygenase-2 mRNA, and to lead to the phosphorylation of glycogen synthase kinase-3.

Useful EP$_4$ receptor antagonists include, for example, those set forth in: U.S. Pat. Nos. 8,158,671, 8,013,159 and 8,003,661.

Additional EP$_4$ receptor antagonists include the compounds described in the following. The structure N-((4'-((3-butyl-5-oxo-1-(2-(trifluoromethyl)phenyl)-1H-1,2,4-triazol-4(5H)-yl)methyl)-[1,1'-biphenyl]-2-yl)sulfonyl)-3-methylthiophene-2-carboxamide is:

and includes pharmaceutically acceptable salts of the above. The structure of (S)-4-(1-(5-chloro-2-(4-fluorophenoxy)benzamido)ethyl)benzoic acid is:

and includes pharmaceutically acceptable salts of the above. The structure of (Z)-7-((1S,2R,5S)-5-(2-([1,1'-biphenyl]-4-yl)ethyl)-2-morpholino-3-oxocyclopentyl)hept-4-enoic acid is:

and includes pharmaceutically acceptable salts of the above. The structure of 4-(4-cyano-2-(2-(4-fluoronaphthalen-1-yl)propanamido)phenyl)butanoic acid is:

and includes pharmaceutically acceptable salts of the above.

An example of an EP$_4$ receptor antagonist useful in the experimental work and methods disclosed herein is described below as Formula IV. The structure of Formula IV is:

(IV)

and includes pharmaceutically acceptable salts of the above.

An example of an EP$_4$ receptor agonist useful in the experimental work disclosed herein is described below as Formula V. The structure of Formula V is:

(V)

and includes pharmaceutically acceptable salts of the above.

In one embodiment, neovascularization (e.g., choroidal neovascularization) is associated with excess levels of vascular endothelial growth factor (VEGF). The terms "excess levels" and the like in the context of concentrations of biological molecules (e.g., VEGF) refer to concentrations which are greater than concentrations found under normal physiological conditions (e.g., in the absence of neovascularization). Methods for determining the concentrations of biological molecules in the subject are well known in the art and include, e.g., biological assays, direct quantification of concentrations, and the like. Accordingly, the phrase "neovascularization is associated with excess levels of VEGF" and the like refer to neovascularization wherein the concentration of VEGF in the subject is greater than the concentration found in the absence of neovascularization. The greater concentration of VEGF can be at the site of neovascularization or in the tissue surrounding the site of neovascularization or associated with it.

The terms "vascular endothelial growth factor," "VEGF" and the like refer in the usual and customary sense to a sub-family of the platelet-derived growth factor family, which is a member of the cystine-knot family of growth factors. VEGF's include, for example, subtypes such as VEGF-A, VEGF-B, VEGF-C, VEGF-D, and the like. VEGF is a signal protein that typically stimulates vasculogenesis and angiogenesis and can contribute to disease when overexpressed. For example, overexpression of VEGF can cause vascular disease in the retina of the eye and other parts of the body. Drugs such as bevacizumab (humanized monoclonal antibody to VEGF-A) can inhibit VEGF and control or slow those diseases.

In one embodiment, administration of an effective amount of the IP receptor antagonist in combination with an effective amount of the $EP_4$ receptor antagonist inhibits (e.g., decreases) the secretion of VEGF. In one embodiment, the secretion of VEGF is inhibited by 10%, 20%, 30%, 40%, 50%, 60%, 70%, 80%, 90%, 95%, or even greater, with respect to the secretion of VEGF in the absence of the administration of the IP receptor antagonist and the $EP_4$ receptor antagonist. Thus, in one embodiment, the concentration of VEGF is decreased due to the decrease in secretion of VEGF.

In one embodiment the neovascularization is choroidal neovascularization (CNV). Accordingly, the phrases "choroidal neovascularization is associated with excess levels of VEGF" and the like refer to choroidal neovascularization wherein the concentration of VEGF in the subject is greater than the concentration found in the absence of choroidal neovascularization. The greater concentration of VEGF can be at the site of choroidal neovascularization or in the tissue surrounding the site of choroidal neovascularization or associated with it.

In one embodiment, the choroidal neovascularization is associated with age-related macular degeneration (e.g., wet type age-related macular degeneration). The terms "age-related macular degeneration," "AMD" and the like refer to a medical condition, typically afflicting older adults (e.g., >=50-yrs age), which results in loss of vision, especially in the macular visual field. The condition typically results from damage to the retina. In the "dry" (nonexudative) form of AMD, cellular debris (i.e., drusen) accumulates between the retina and the choroid, and the retina can become detached. In the more severe "wet" (exudative) form, blood vessels emerge from the choroid in the choriocapillaris through Bruch's membrane. This can ultimately lead to blood and protein leakage below the macula. Bleeding, leaking and scarring from these blood vessels can eventually cause irreversible damage to the photoreceptors. Moreover, the retina can become detached.

In one embodiment, the CNV is induced by exposure to a laser. In one embodiment, the IP receptor antagonist is capable of reducing VEGF levels (e.g., reducing VEGF levels in the choroid or in tissue associated with the choroid). In one embodiment, the $EP_4$ receptor antagonist is capable of reducing VEGF levels (e.g., reducing VEGF levels in the choroid or in tissue associated with the choroid).

In one embodiment, the IP receptor antagonist has the structure of Formula (II), and the neovascularization is associated with excess levels of VEGF. In one embodiment, the IP receptor antagonist having the structure of Formula (II) and an $EP_4$ receptor antagonist in combination inhibit secretion of VEGF in the subject. In one embodiment, the neovascularization is choroidal neovascularization. In one embodiment, the choroidal neovascularization is associated with wet-type age-related macular degeneration. In one embodiment, the choroidal neovascularization is laser-induced.

Further to any embodiment disclosed above, in one embodiment the $EP_4$ receptor antagonist is Formula (IV).

II. Pharmaceutical Compositions

In another aspect, there is provided a pharmaceutical composition including an IP receptor antagonist in combination with an $EP_4$ receptor antagonist, further in combination with a pharmaceutically acceptable excipient (e.g., carrier). In one embodiment, the pharmaceutical composition is an ophthalmic pharmaceutical composition. The term "ophthalmic pharmaceutical composition" refers to a pharmaceutical composition suitable for administration to the eye. The "ophthalmic pharmaceutical composition" may be formulated for delivery of an IP receptor antagonist in combination with an $EP_4$ receptor antagonist to the choroid of a subject.

The phrases "pharmaceutically acceptable excipient," "pharmaceutically acceptable carrier" and the like as used herein refer to pharmaceutical excipients, e.g., pharmaceutically, physiologically, acceptable organic or inorganic carrier substances suitable for administration, and which do not deleteriously react with the active agent. In one embodiment, a pharmaceutical composition can be sterilized and/or mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds disclosed herein. The term "ophthalmic pharmaceutically acceptable excipient" refers to a pharmaceutically acceptable excipient suitable for administration to the eye.

The term "pharmaceutically acceptable salt" is meant to include salts of the active compounds that are prepared with relatively nontoxic acids or bases, depending on the particular substituents found on the compounds described herein. When compounds disclosed herein contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds disclosed herein contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or qalacturonic acids and the like (see, for example, Berge et al., *Journal of Pharmaceutical Science,* 1977, 66, 1-19). Certain specific compounds disclosed herein may contain both basic and acidic functionalities that allow the compounds to be converted into either base or acid addition salts.

The compounds disclosed herein may exist as salts, such as with pharmaceutically acceptable acids. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

In addition to salt forms, embodiments disclosed herein provide compounds in a prodrug form. Prodrugs of the compounds described herein are those compounds that readily undergo chemical changes under physiological conditions to provide certain of the compounds disclosed herein. Additionally, prodrugs can be converted to certain compounds disclosed herein by chemical or biochemical methods in an ex vivo environment. For example, prodrugs can be slowly converted to certain compounds disclosed herein when placed in a transdermal patch reservoir with a suitable enzyme or chemical reagent.

Certain compounds disclosed herein can exist in unsolvated forms as well as solvated forms, including hydrated forms. In general, the solvated forms are equivalent to unsolvated forms and are encompassed within the scope of the present invention. Certain compounds disclosed herein may exist in multiple crystalline or amorphous forms. In general, all physical forms are equivalent for the uses contemplated by the present invention and are intended to be within the scope of the present invention.

Certain compounds disclosed herein possess asymmetric carbon atoms (optical centers) or double bonds; the racemates, diastereomers, tautomers, geometric isomers, and individual isomers are encompassed within the scope of the present invention. The compounds disclosed herein do not include those that are known in the art to be too unstable to synthesize and/or isolate.

The compounds disclosed herein may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I), or carbon-14 ($^{14}$C). All isotopic variations of the compounds disclosed herein, whether radioactive or not, are encompassed within the scope of the present invention.

The compounds disclosed herein can be administered alone or can be coadministered to the subject. Coadministration is meant to include simultaneous or sequential administration of the compounds individually or in combination (more than one compound). The preparations can also be combined, when desired, with other active substances (e.g. to reduce metabolic degradation). Accordingly, the phrases "administering to said subject an effective amount of an IP receptor antagonist in combination with an effective amount of an $EP_4$ receptor antagonist" and the like mean that the IP receptor antagonist and the $EP_4$ receptor antagonist can be administered simultaneously or sequentially.

In one embodiment, the pharmaceutical composition includes an IP receptor antagonist and an $EP_4$ receptor antagonist, each independently at a concentration in the range of about 0.01% to 1.00% (w/v). In one embodiment, the concentration of the IP receptor antagonist is about 0.01%, 0.02%, 0.03%, 0.04%, 0.05%, 0.06%, 0.07%, 0.08%, 0.09%, 0.10%, 0.11%, 0.12%, 0.13%, 0.14%, 0.15%, 0.16%, 0.17%, 0.18%, 0.19%, 0.20%, 0.30%, 0.40%, 0.50%, 0.60%, 0.70%, 0.80%, 0.90%, or 1.00% (w/v), or even greater. In one embodiment, the concentration of the $EP_4$ receptor antagonist is about 0.01%, 0.02%, 0.03%, 0.04%, 0.05%, 0.06%, 0.07%, 0.08%, 0.09%, 0.10%, 0.11%, 0.12%, 0.13%, 0.14%, 0.15%, 0.16%, 0.17%, 0.18%, 0.19%, 0.20%, 0.30%, 0.40%, 0.50%, 0.60%, 0.70%, 0.80%, 0.90%, or 1.00% (w/v), or even greater.

A. Formulations

The compounds disclosed herein can be prepared and administered in a wide variety of ophthalmic, oral, parenteral, and topical dosage formulations. Thus, the compounds disclosed herein can be administered by injection (e.g. intravenously, intramuscularly, intracutaneously, subcutaneously, intraduodenally, or intraperitoneally). Also, the compounds described herein can be administered by inhalation, for example, intranasally. Additionally, the compounds disclosed herein can be administered transdermally or by ocular instillation. Multiple routes of administration (e.g., intramuscular, oral, transdermal, ocular instillation) are contemplated that can be used to administer the compounds disclosed herein. Accordingly, embodiments of the present invention also provide pharmaceutical compositions (e.g., an ophthalmic pharmaceutical composition) which include a pharmaceutically acceptable carrier or excipient and one or more compounds (e.g., IP receptor antagonist and $EP_4$ receptor antagonist).

In another aspect, there is provided an ophthalmic pharmaceutical formulation. An "ophthalmic pharmaceutical formulation" includes an ophthalmic pharmaceutical composition and is formulated to be administered to the eye. In one embodiment, the ophthalmic pharmaceutical formulation is instilled in the eye. In one embodiment, the ophthalmic pharmaceutical formulation is injected into the eye, or into tissue surrounding or associated with the eye.

In one embodiment, the ophthalmic pharmaceutical formulation includes an IP receptor antagonist and an $EP_4$ receptor antagonist, each independently at a concentration in the range of about 0.01% to 1.00% (w/v). In one embodiment, the concentration of the IP receptor antagonist is about 0.01%, 0.02%, 0.03%, 0.04%, 0.05%, 0.06%, 0.07%, 0.08%, 0.09%, 0.10%, 0.11%, 0.12%, 0.13%, 0.14%, 0.15%, 0.16%, 0.17%, 0.18%, 0.19%, 0.20%, 0.30%, 0.40%, 0.50%, 0.60%, 0.70%, 0.80%, 0.90%, or 1.00% (w/v), or even greater. In one embodiment, the concentration of the $EP_4$ receptor antagonist is about 0.01%, 0.02%, 0.03%, 0.04%, 0.05%, 0.06%, 0.07%, 0.08%, 0.09%, 0.10%, 0.11%, 0.12%, 0.13%, 0.14%, 0.15%, 0.16%, 0.17%, 0.18%, 0.19%, 0.20%, 0.30%, 0.40%, 0.50%, 0.60%, 0.70%, 0.80%, 0.90%, or 1.00% (w/v), or even greater.

The ophthalmic pharmaceutical formulation can include buffers to adjust the pH to a desirable range for ophthalmic use. Generally, a pH of around 6-8 is desired, and in certain ophthalmic pharmaceutical formulations a pH of 7.4 is desired. Many buffers including salts of inorganic acids such as phosphate, borate, and sulfate are known. In one embodiment, the buffer maintains the pH of the ophthalmic pharmaceutical formulation in the range of about 6.5 to 7.5. In one embodiment, the buffer maintains the pH of the ophthalmic pharmaceutical formulation in the range of about 7.0 to 7.4.

In one embodiment, the ophthalmic pharmaceutical formulation includes one or more viscosity-enhancing agents, or thickening agents. Thickening agents are used for a variety of reasons, ranging from improving the form of the formulation for convenient administration to improving the contact with the eye to improve bioavailability. The viscosity-enhancing agent may comprise a polymer containing hydrophilic groups such as monosaccharides, polysaccharides, ethylene oxide groups, hydroxyl groups, carboxylic acids or other charged functional groups. While not intending to limit the scope of the invention, some examples of useful viscosity-enhancing agents are sodium carboxymethylcellulose, hydroxypropyl methylcellulose, povidone, polyvinyl alcohol, and polyethylene glycol. In one embodiment, viscosity-enhancing agents are employed at a level between about 0.01% and about 2% (w/v).

In one embodiment, the ophthalmic pharmaceutical formulation includes one or more tonicity agents useful to adjust the ophthalmic pharmaceutical formulation to the desired isotonic range. Tonicity agents are well known in the art and some examples include glycerin, mannitol, sorbitol, sodium chloride, and other electrolytes. In one embodiment, the concentration of tonicity agent is in the range of about 0.1 to 2.00% (w/v). In one embodiment, the concentration of tonicity agent is in the range of about 1.15 to 1.30% (w/v). In one embodiment, the concentration of tonicity agent is about 0.10%, 0.20%, 0.30%, 0.40%, 0.50%, 0.60%, 0.70%, 0.80%, 0.90%, 1.00%, 1.10%, 1.20%, 1.30%, 1.40%, 1.50%, 1.60%, 1.70%, 1.80%, 1.90%, or 2.00%. In one embodiment, the concentration of tonicity agent is about 1.15%, 1.16%, 1.17%, 1.18%, 1.19%, 1.20%, 1.21%, 1.22%, 1.23%, 1.24%, 1.25%, 1.26%, 1.27%, 1.28%, 1.29%, or 1.30% (w/v).

In one embodiment, the ophthalmic pharmaceutical formulation includes a solubilizer (e.g., surfactant or other appropriate co-solvent) in order to facilitate solubilization of one or more components of the ophthalmic pharmaceutical formulation. Such solubilizers include Polysorbate 20, 60, and 80, Pluronic F-68, F-84, and P-103, cyclodextrin, hydroxy-beta-cyclodextrin, solutol, polyoxyethylene 40 stearate, and polyoxyl 35 castor oil. Such solubilizers can be employed at a level between about 0.01% and about 2% by weight. In one embodiment, the solubilizer is present in the range of about 0.01% to 0.20% (w/v). In one embodiment, the solubilizer is present at 0.01%, 0.02%, 0.03%, 0.04%, 0.05%, 0.06%, 0.07%, 0.08%, 0.09%, 0.10%, 0.11%, 0.12%, 0.13%, 0.14%, 0.15%, 0.16%, 0.17%, 0.18%, 0.19%, or 0.20% (w/v). In one embodiment, the solubilizer is polysorbate 80.

In one embodiment, the ophthalmic pharmaceutical formulation includes a preservative. In one embodiment, the preservative is benzalkonium chloride, chlorine dioxide, chlorobutanol, thimerosal, phenylmercuric acetate, or phenylmercuric nitrate. In one embodiment, the preservative is present at a concentration in the range of about 0.01% to 0.05% (w/v). In one embodiment, the preservative is present at a concentration in the range of about 0.015% to 0.025% (w/v). In one embodiment, the concentration of the preservative is about 0.015%, 0.016%, 0.017%, 0.018%, 0.019%, 0.020%, 0.021%, 0.022%, 0.023%, 0.024%, or 0.025% (w/v). In one embodiment, the preservative is benzalkonium chloride.

The compositions disclosed herein may additionally include components to provide sustained release and/or comfort. Such components include high molecular weight, anionic mucomimetic polymers, gelling polysaccharides, and finely-divided drug carrier substrates. These components are discussed in greater detail in U.S. Pat. Nos. 4,911,920; 5,403,841; 5,212,162; and 4,861,760, the entire contents of each of which are incorporated herein by reference in their entirety and for all purposes.

B. Effective Dosages

Pharmaceutical compositions contemplated herein include compositions wherein the active ingredient is contained in an effective amount, i.e., in an amount effective to achieve its intended purpose. An "effective amount" is an amount sufficient to accomplish a stated purpose (e.g., achieve the effect for which it is administered, treat a disease, reduce one or more symptoms of a disease or condition). An example of an "effective amount" is an amount sufficient to contribute to the treatment, prevention, or reduction of a symptom or symptoms of a disease, which can be referred to as a "therapeutically effective amount." A "reduction" of a symptom or symptoms (and grammatical equivalents of this phrase) means decreasing of the severity or frequency of the symptom(s), or elimination of the symptom(s). The actual amount effective for a particular application will depend, inter alia, on the condition being treated. For example, when administered in methods to treat neovascularization (e.g., choroidal neovascularization), such compositions will contain amounts of active ingredients effective to achieve the desired result (e.g. decreasing the extent of neovascularization in a subject).

The dosage and frequency (single or multiple doses) of compounds administered can vary depending upon a variety of factors, including route of administration; size, age, sex, health, body weight, body mass index, and diet of the recipient; nature and extent of symptoms of the disease being treated (e.g., the disease responsive to an IP receptor antagonist); presence of other diseases or other health-related problems; kind of concurrent treatment; and complications from any disease or treatment regimen. Other therapeutic regimens or agents can be used in conjunction with the methods and compounds disclosed herein.

For any compound described herein or combination thereof, the therapeutically effective amounts can be initially determined from cell culture assays. Target concentrations will be those concentrations of active compound(s) that are capable of decreasing neovascularization (e.g., choroidal neovascularization) as measured, for example, using methods known in the art.

Therapeutically effective amounts for use in humans may be determined from animal models. For example, a dose for humans can be formulated to achieve a concentration that has been found to be effective in animals. The dosage in humans can be adjusted by monitoring neovascularization (e.g., choroidal neovascularization) and adjusting the dosage upwards or downwards, as described above.

Dosages may be varied depending upon the requirements of the subject and the compound being employed. The dose administered to a subject, in the context of certain embodiments disclosed herein, should be sufficient to effect a beneficial therapeutic response in the subject over time. The size of the dose also will be determined by the existence, nature, and extent of any adverse side effects. Generally, treatment is initiated with smaller dosages, which are less than the optimum dose of the compound. Thereafter, the dosage is increased by small increments until the optimum effect under circumstances is reached.

Dosage amounts and intervals can be adjusted individually to provide levels of the administered compounds effective for the particular clinical indication being treated. This will provide a therapeutic regimen that is commensurate with the severity of the individual's disease state.

Utilizing the teachings provided herein, an effective therapeutic treatment regimen can be planned that does not cause substantial toxicity and yet is entirely effective to treat the clinical symptoms demonstrated by the particular patient. This planning should involve the careful choice of active compound by considering factors such as compound potency, relative bioavailability, patient body weight, presence and severity of adverse side effects, preferred mode of administration, and the toxicity profile of the selected agent.

C. Toxicity

The ratio between toxicity and therapeutic effect for a particular compound is its therapeutic index and can be expressed as the ratio between $LD_{50}$ (the amount of compound lethal in 50% of the population) and $ED_{50}$ (the amount of compound effective in 50% of the population). Compounds that exhibit high therapeutic indices are preferred. Therapeutic index data obtained from cell culture assays and/or animal studies can be used in formulating a range of dosages for use in humans. The dosage of such compounds preferably lies within a range of plasma concentrations that include the $ED_{50}$ with little or no toxicity. The dosage may vary within this range depending upon the dosage form employed and the route of administration utilized. See, e.g. Fingl et al., *In: The Pharmacological Basis of Therapeutics*, Ch. 1, p. 1, 1975. The exact formulation, route of administration, and dosage can be chosen by the individual physician in view of the patient's condition and the particular method in which the compound is used.

The abbreviations used herein have their conventional meaning within the chemical and biological arts. The chemical structures and formulae set forth herein are constructed according to the standard rules of chemical valency known in the chemical arts.

III. Examples

Example 1

Figure 1A:
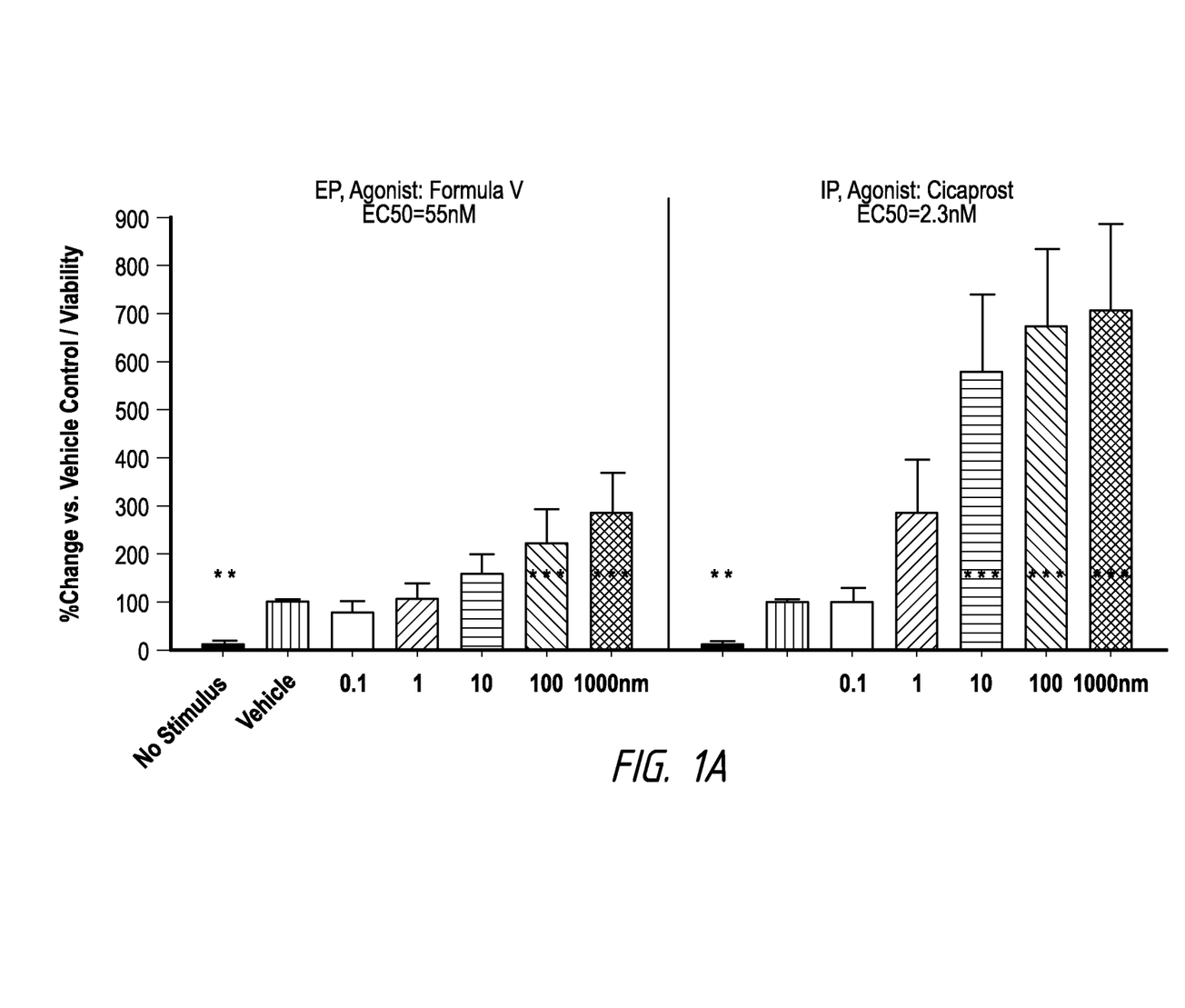
FIG. 1A is a histogram depicting $EP_4$ receptor agonist Formula V (left panel) and IP receptor agonist Cicaprost (right panel) dose dependently inducing VEGF secretion in TNFα-stimulated human macrophages. $p<0.01$, * $p<0.001$ compared to the vehicle control. Average $EC_{50}$ is 55 nM for Formula V, and 2.3 nM for Cicaprost, n=4 donors. Histogram ordering (both panels, left to right): No stimulus; vehicle; 0.1 nM; 1 nM; 10 nM; 100 nM; 1000 nM of agonist.

Investigation of VEGF Secretion and Inhibition in TNFα-Stimulated Human Macrophage A TNFα-stimulated human macrophage system was employed to assess the effect of $EP_4$ receptor agonist and IP receptor agonist on induction of VEGF secretion. VEGF plays an important role in neovascularization. As depicted in the histograms of FIG. 1A, in TNFα-stimulated human macrophages, prostanoid receptor agonists Formula V (on $EP_4$) and Cicaprost (on IP) are both potent inducers of VEGF secretion.

Figure 1B:
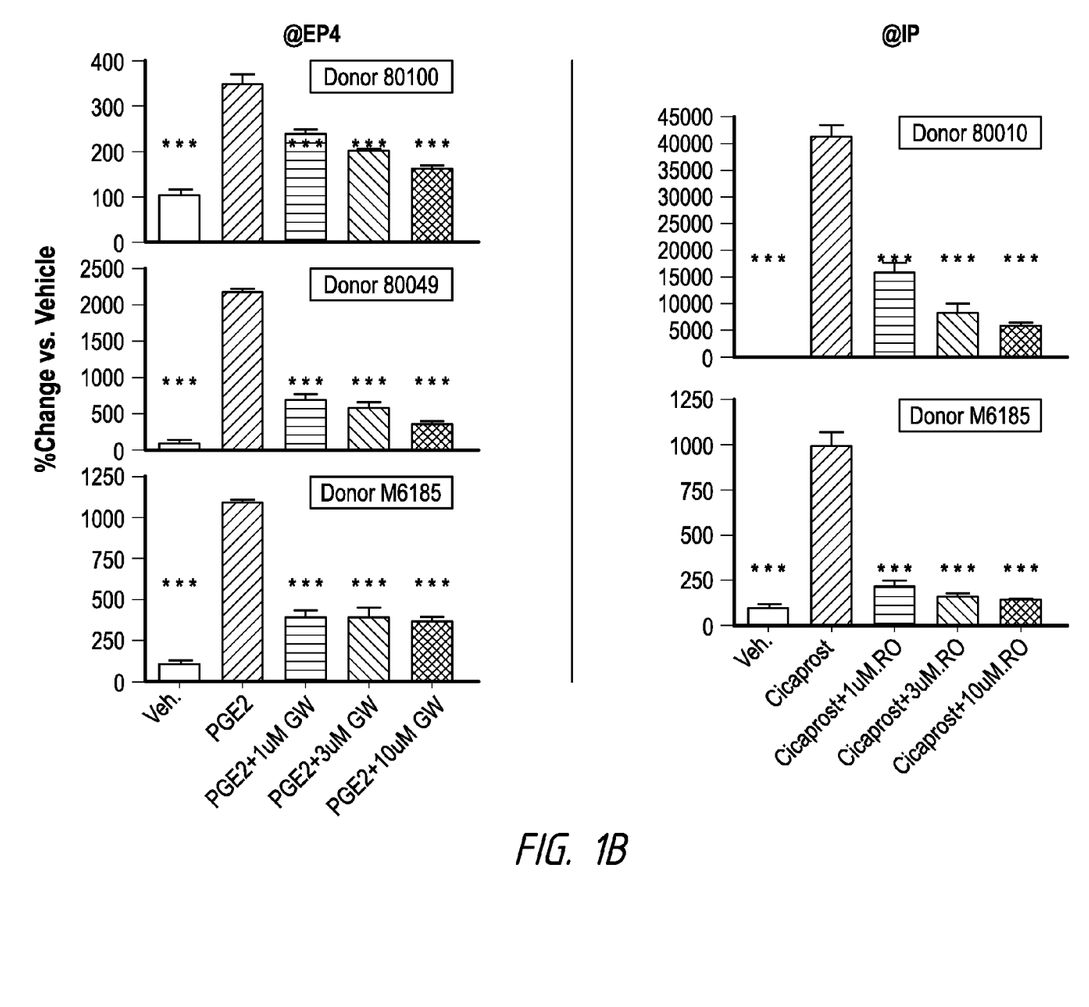
FIG. 1B provides histograms depicting $EP_4$ receptor antagonist Formula IV (left panels) and IP receptor antagonist Formula I (right panels) dose dependently inhibiting 100 nM $PGE_2$ (left panels, n=3) or 100 nM Cicaprost-induced (right panels, n=2) VEGF secretion in TNFα-stimulated human macrophages from individual donors. *** $p<0.001$ compared to $PGE_2$ or Cicaprost control. Histogram ordering (left panels, left to right): Vehicle; $PGE_2$; $PGE_2$+1 µM Formula IV; $PGE_2$+3 µM Formula IV; $PGE_2$+10 µM Formula IV. Histogram ordering (right panels, left to right): Vehicle; Cicaprost; Cicaprost+1 µM Formula I; Cicaprost+3 µM Formula I; Cicaprost+10 µM Formula I.

The effect on TNFα-stimulated human macrophages, obtained from individual donors, of administration of $EP_4$ receptor antagonist and IP receptor antagonist was investigated. Specifically, FIG. 1B (left panel) depicts histograms showing effect of Formula IV (on $EP_4$) on VEGF secretion in TNFα-stimulated human macrophages induced with 100 nM $PGE_2$ (n=3). FIG. 1B (right panels) depicts histograms showing effect of selective prostanoid receptor antagonists Formula I (on IP) in TNFα-stimulated human macrophages induced with 100 nM cicaprost (n=2).

Example 2

Cellular Dielectric Spectroscopy Studies

Figure 2A:
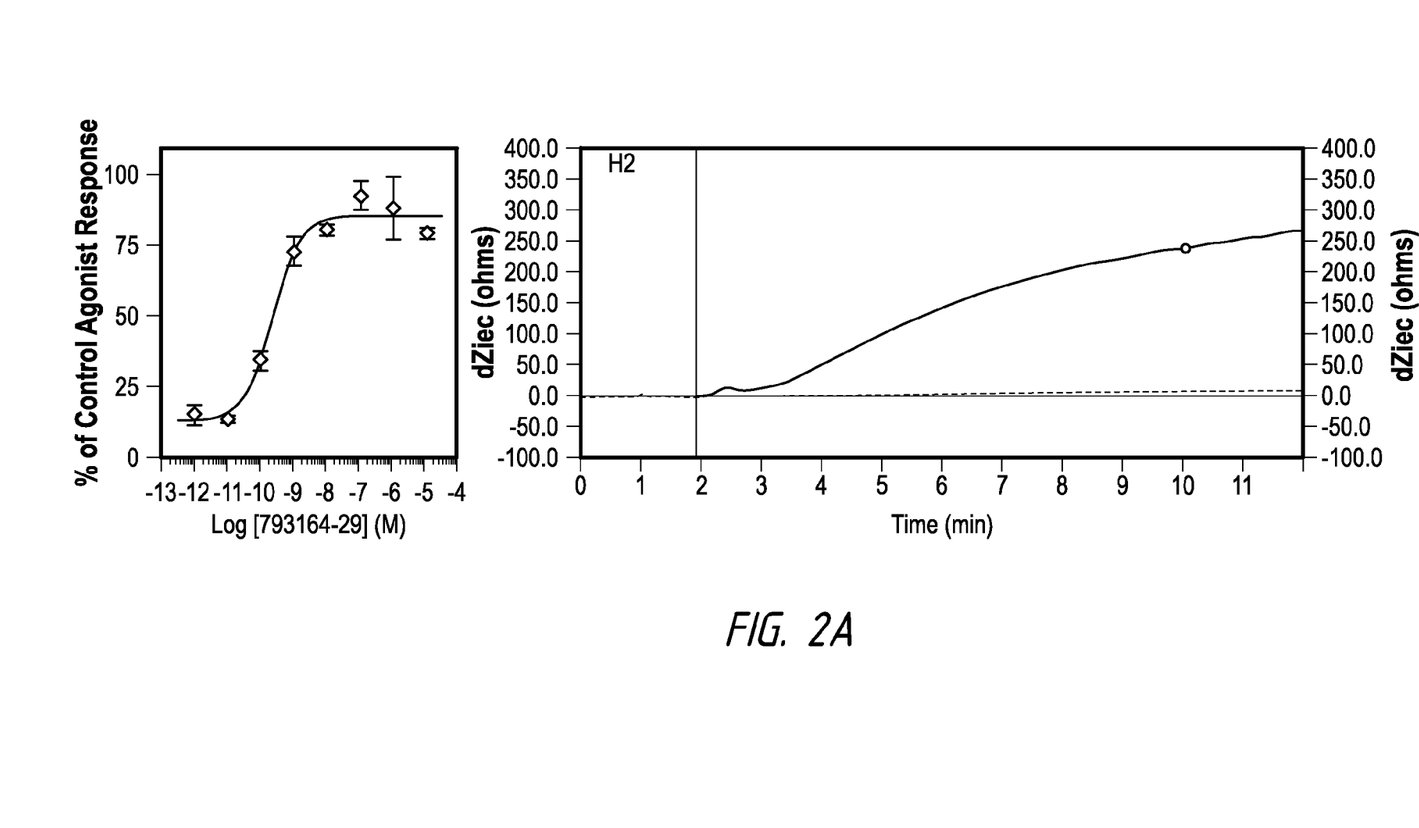
Figure 2B:
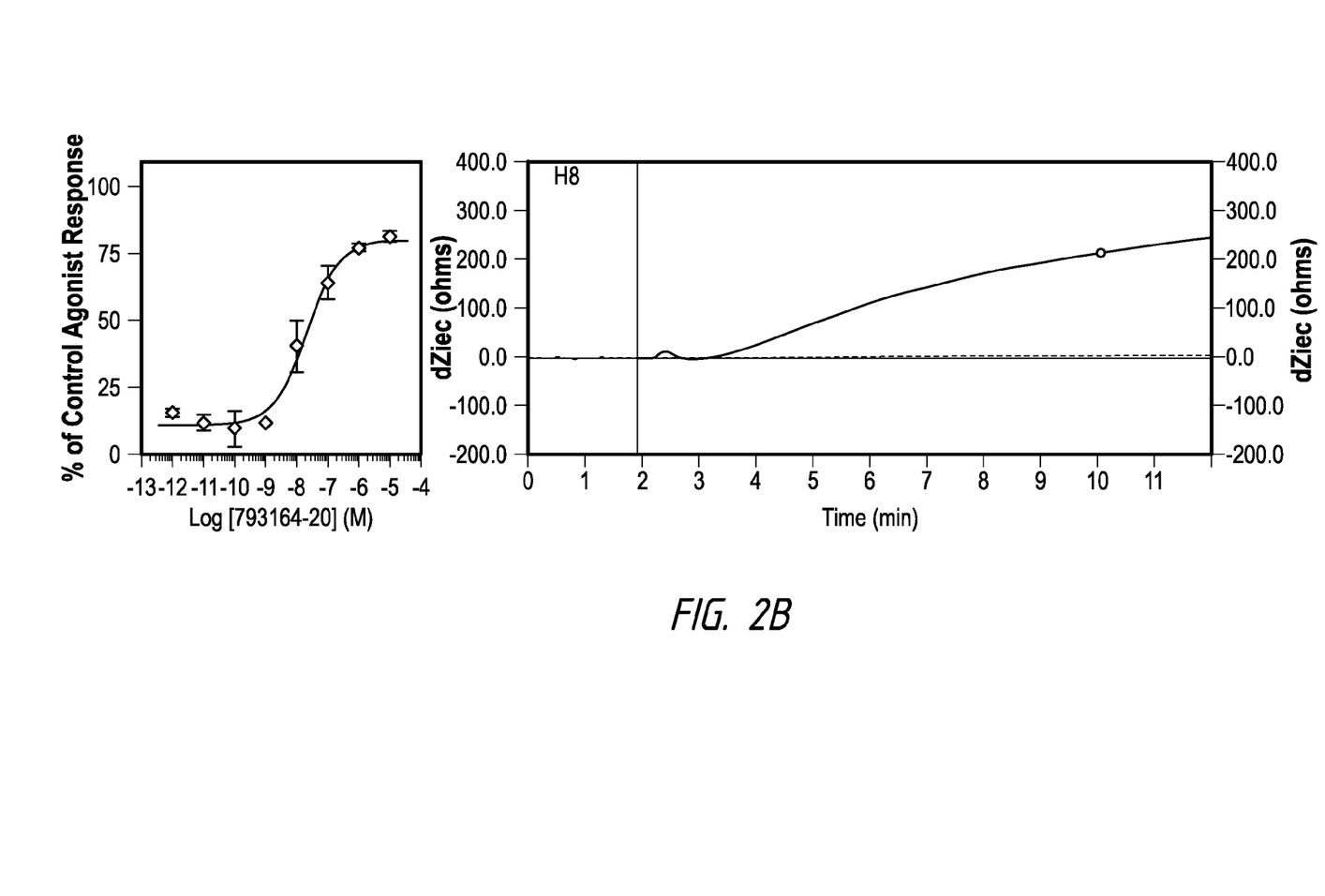

Cellular dielectric spectroscopy, as known in the art, was employed to determine $EC_{50}$ levels for $EP_4$ agonist and IP agonist in human retinal microvascular endothelial cells (HRMECs). As shown in FIG. 2A, the $EC_{50}$ is observed to be 0.23 nM for the $EP_4$ agonist "PDA-130"=Formula V (See e.g., Foudi et al., 2008, Br J Pharmacol. 154(8):1631-9. As shown in FIG. 2B, the $EC_{50}$ for the IP agonist cicaprost is observed to be 18 nM.

Cellular Dielectric Spectroscopy (CDS) is a label-free technology to measure the changes in impedance of cells in response to receptor stimulation. HRMEC cells were seeded at on 96 well plates (CDS plates) coated with fibronectin and incubated for 24 hrs at 37° C., 5% CO2. On the day of the experiment, the culture medium was replaced by HBSS, BSA 1% and incubated for 1 h at 28° C. Compounds were then added and the signal was monitored for 10 minutes at 28° C. Compounds were tested at the following final concentrations in assay buffer containing 0.1% DMSO: 1E-12, 1E-11, 1E-10, 1E-9, 1E-8, 1E-7, 1E-6, and 1E-5M. The background signal (buffer only) was systematically subtracted to the signal in order to determine the specific signal. The effect of $EP_4$ agonist Formula V and IP agonist Cicaprost were normalized to the signal of the positive control $PGE_2$ at 10 μM. All data were generated in duplicate.

Example 3

In Vivo Investigation of Laser-Induced Choroidal Neovascularization

A laser-induced model of CNV was employed, as known in the art, to determine whether blockade of IP and $EP_4$ receptor is superior to blockade of IP receptors alone in ameliorating the effects of laser-induced CNV. See e.g., Francois et al., 1975, *Am. J. Ophthalmol.* 79:206-210; Edelman & Castro, 2000, *Exp. Eye Res.* 71:523-533; Goody, R. J., et al., 2011, *Exp. Eye. Research* 92:464-472.

Figure 3A:
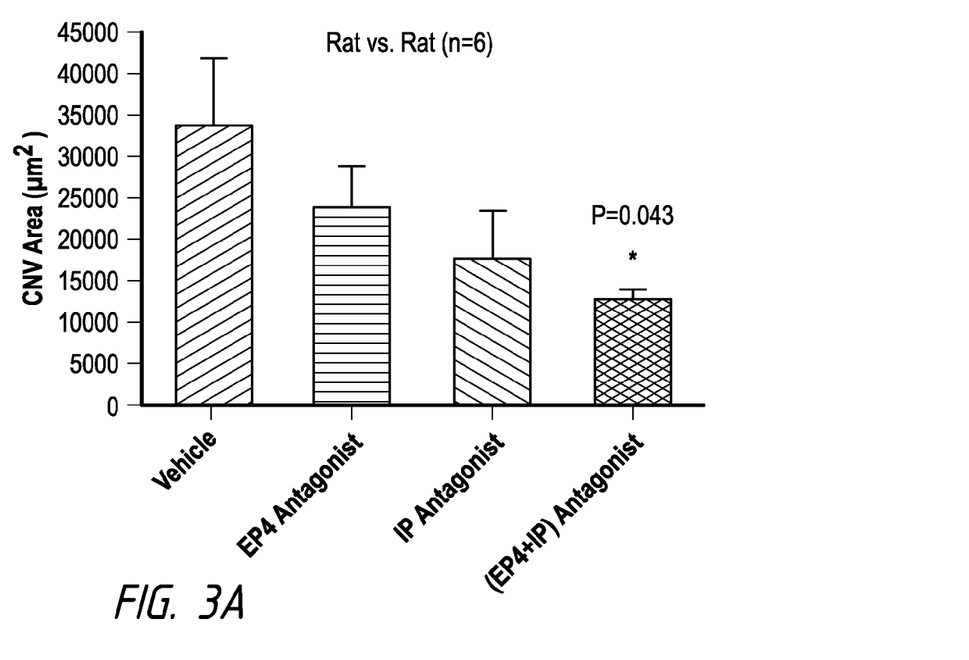
FIG. 3A: CNV area (µm²) rat vs. rat comparison, n=6. 230933.
Figure 3B:
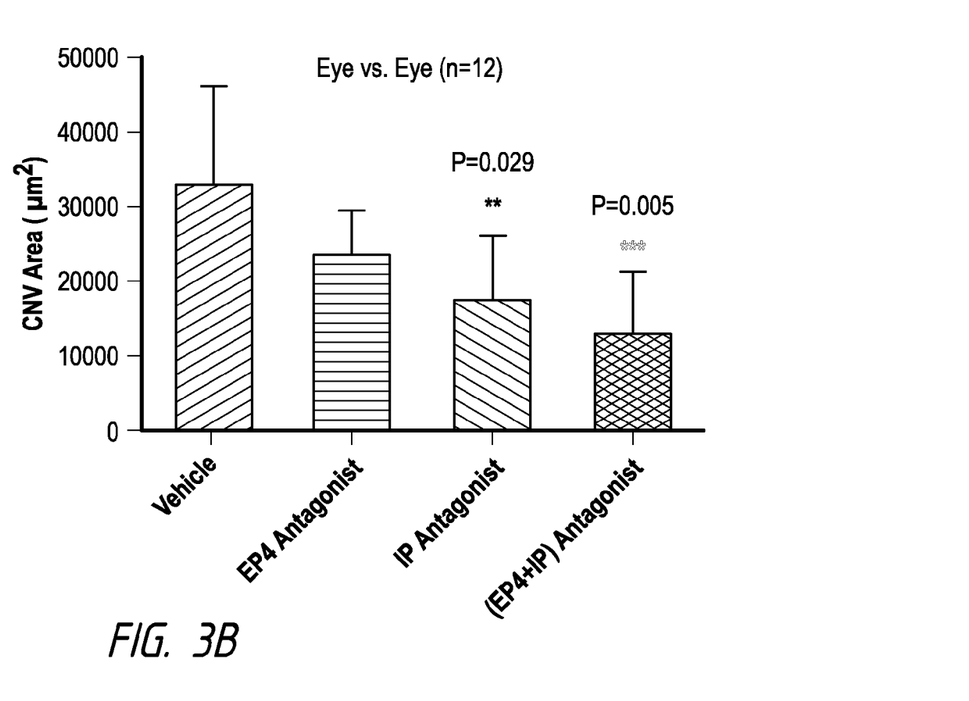
FIG. 3B: CNV area (µm²) eye vs. eye comparison, n=12. Formula II.
Figure 3C:
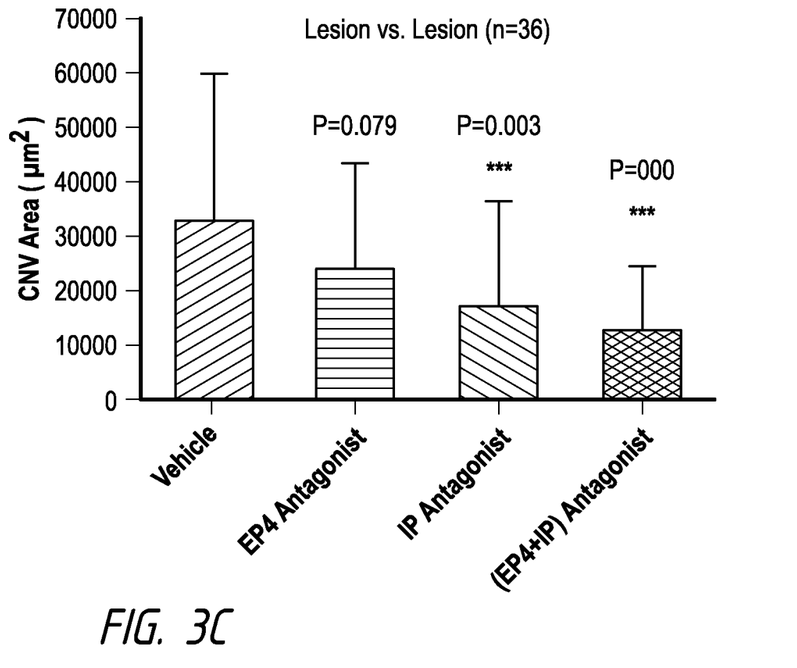

Test rats were administered laser treatment after which vehicle (50% propylene glycol in $H_2O$), or IP receptor antagonist Formula II or $EP_4$ receptor antagonist Formula IV, alone or in combination, were administered. The area of subsequently identified CNV was quantified by methods known in the art. As shown in FIG. 3A, the area (μm$^2$) of CNV was significantly reduced per test subject after administration of the combination of antagonists. As depicted in FIG. 3B, the area of CNV was also reduced as judged by a comparison of each eye. Moreover, as depicted in FIG. 3C, the area of CNV was reduced on a per lesion basis.

What is claimed is:

1. A method for decreasing neovascularization in a subject in need thereof, comprising administering to said subject an effective amount of an IP receptor antagonist in combination with an effective amount of an $EP_4$ receptor antagonist, thereby decreasing said neovascularization.

2. The method of claim 1, wherein said neovascularization is associated with excess levels of vascular endothelial growth factor (VEGF).

3. The method of claim 2, wherein administering said IP receptor antagonist in combination with said $EP_4$ receptor antagonist inhibits secretion of VEGF in said subject.

4. The method of claim 3, wherein said neovascularization is choroidal neovascularization.

5. The method of claim 4, wherein said choroidal neovascularization is associated with age-related macular degeneration of the wet type.

6. The method of claim 4, wherein said choroidal neovascularization is the result of physical trauma, chemical trauma, or secondary to cardiovascular disease.

7. The method of claim 1, wherein said IP receptor antagonist has the structure of Formula (II):

8. The method of claim 7, wherein said neovascularization is associated with excess levels of vascular endothelial growth factor (VEGF).

9. The method of claim 8, wherein administering said IP receptor antagonist in combination with said $EP_4$ receptor antagonist inhibits secretion of VEGF in said subject.

10. The method of claim 7, wherein said neovascularization is choroidal neovascularization.

11. The method of claim 10, wherein said choroidal neovascularization is associated with age-related macular degeneration of the wet type.

12. The method of claim 10, wherein said choroidal neovascularization is laser induced.

13. The method of any one of claims 1 to 12, wherein said $EP_4$ receptor antagonist has the structure of Formula (IV):

14. A pharmaceutical composition comprising an IP receptor antagonist, an $EP_4$ receptor antagonist and a pharmaceutically acceptable excipient.

15. An ophthalmic pharmaceutical formulation comprising an ophthalmic pharmaceutical composition and an ophthalmic pharmaceutically acceptable excipient, said ophthalmic pharmaceutical composition comprising an IP receptor antagonist and an $EP_4$ receptor antagonist.

* * * * *